US008450389B1

(12) United States Patent
Barefoot

(10) Patent No.: US 8,450,389 B1
(45) Date of Patent: May 28, 2013

(54) SYSTEM FOR SOLIDIFICATION OF LIQUID MEDICAL WASTE

(75) Inventor: Quint Barefoot, McLeansville, NC (US)

(73) Assignee: Zappa-Tec LLC, McLeansville, NC (US)

( * ) Notice: Subject to any disclaimer, the term of this patent is extended or adjusted under 35 U.S.C. 154(b) by 502 days.

(21) Appl. No.: 12/752,688

(22) Filed: Apr. 1, 2010

(51) Int. Cl.
*C08K 3/16* (2006.01)
*C08K 3/36* (2006.01)

(52) U.S. Cl.
USPC ................ 523/122; 523/220; 524/1; 524/492

(58) Field of Classification Search
USPC ............... 523/122, 220; 524/1, 492; 428/402, 428/500
See application file for complete search history.

(56) References Cited

U.S. PATENT DOCUMENTS 5,391,351 A 2/1995 Kaufman ........................ 422/28
6,797,857 B2 9/2004 Tanhehco ...................... 604/368
7,291,674 B2 11/2007 Kang et al. .................. 525/54.1

*Primary Examiner* — Kriellion Sanders
(74) *Attorney, Agent, or Firm* — MacCord Mason PLLC

(57) ABSTRACT

The invention includes a system for solidification of liquid medical waste for use in connection with a vessel configured to receive an aqueous liquid to be solidified. The system includes an absorbent composition including a plurality of surface cross-linked superabsorbent particles and a plurality of second particles. Additionally, a soluble packet may be included so that the absorbent composition is released upon dissolution of the packet. The invention also includes a liquid solidification system for reducing gel block and a method of solidifying liquid medical waste.

13 Claims, 3 Drawing Sheets

SYSTEM FOR SOLIDIFICATION OF LIQUID MEDICAL WASTE

FIELD OF TECHNOLOGY

Conventional medical waste solidifiers are contained in bottles or packets and are used successfully in many hospitals and surgical centers throughout the country. However, there is inconvenience, considerable cost, and risk associated with post procedure handling of suction canister waste, leading to a need for a safer, more complete, and a more efficient solidification system.

BACKGROUND

Liquid medical waste is flowed into medical waste containers. The liquid medical waste is deposited under the influence of a suction, which directs the liquid through a conduit. The waste is usually an aqueous fluid mixture of saline, blood, urine, and/or other bodily fluids. Regulations require that the liquid be converted to a solidified form prior to transport in order to minimize the possibility of hazardous waste being spilled.

While solidifiers have attempted to reach firm solidification, where no fluids will spill when the container is turned on its side, a problem with "gel block" has persisted. Development of "gel block" prohibits firm solidification. "Gel block" occurs when the inflowing aqueous mixture becomes solidified and sections off portions of the fluid so that it can not reach available solidifier. When gel block occurs, the aqueous fluid does not firmly and completely solidify and spillage during transport is problematic.

Previously, the problem of "gel block" has been addressed in a variety of ways. Various solidifiers with different densities have been combined so that the solidifier will migrate to specific levels or zones of the fluid. However, weighted solidifiers take some time to reach their separated levels, and the use of swifter solidifiers with this system still presents problems with "gel block." Additionally, the speed with which the fluid is introduced and the timing of the release of weighted solidifier is extremely important if the weighted solidifier is to inhibit "gel block."

Superabsorbants are known in the art as water-swellable, water-insoluble, organic or inorganic material capable of absorbing at least about 100 times its weight and up to about 300 times its weight in an aqueous solution. Superabsorbent polymers are cross-linked, neutralized polymers which are capable of absorbing large amounts of aqueous liquids and body fluids, such as urine or blood, with swelling and the formation of hydrogels, and of retaining them under a certain pressure in accordance with the general definition of superabsorbent. The main use for internally cross-linked superabsorbent polymers has been in sanitary articles.

The trend in sanitary articles, for comfort and sanitation reasons, has been to make them smaller and reduce their size. To do this, much of the fluff fiber in these articles has been removed and more superabsorbent polymer has been added. With less structure provided, more superabsorbent polymer is needed in sanitary articles along with a higher gel strength. However, increasing gel strength in cross-linked superabsorbent polymers often results in less polymer swellability, permeability and retention capacity. U.S. Pat. No. 7,291,674 to Kang addresses surface cross-linking superabsorbent polymers in order to retain liquid retention, permeability, and gel bed strength when superabsorbent polymer is increased in percent by weight based on the absorbent structure.

Additionally, it is known in the art to add non-polymeric particles to internally cross-linked superabsorbent polymers in order to increase the swellability of the superabsorbent polymers. In fiber optic applications, the cables are coated with a mixture of superabsorbent polymer and non-polymeric silica particles. If the cable covering is breached and fluid seeps inside, the mixture leads to "gel block" and acts as a gelling agent where the suberabsorbent polymers have enhanced swellability so that they water block. In such an application gel block is desired and the particle mixture is designed to achieve gel block as a desired end result.

While the advancements of absorbents, as discussed above, have increased the swellabilty and strength of superabsorbent polymers, they do not assist with use in the solidification of liquid medical waste due to persistent problems with "gel block."

SUMMARY OF THE INVENTION

The present invention fulfills one or more of these needs in the art by providing an absorbent composition that may be used in connection with a vessel configured to receive an aqueous liquid to be solidified. The composition includes a population of superabsorbent polymer particles and a plurality of second particles. The superabsorbent polymer particles have diameters and surfaces and are cross-linked internally and on their surfaces. The second particles have diameters that are substantially smaller than the diameters of the superabsorbent polymer particles. The references to "diameter" are not meant to imply a spherical shape for either particle, but to aid in indicating the differing sizes.

The second particles may be inorganic non-polymeric particles and may be electrostatically attracted to the surfaces of the superabsorbent polymer particles. The second particles may be fumed silica.

Additionally, the absorbent composition may include a sanitizer. The sanitizer may be granular chlorine.

Another embodiment includes a system for solidification of liquid medical waste for use in connection with a vessel configured to receive an aqueous liquid to be solidified. The system includes an absorbent composition and a packet enclosing the absorbent composition. The absorbent composition is granular and includes a plurality of surface cross-linked superabsorbent particles and a plurality of second particles. The packet is at least partially soluble in the aqueous liquid to be solidified so that the absorbent composition is released upon dissolution of the packet. The packet may be made of dissolvable polyvinyl alcohol.

The plurality of second particles become interspersed between the surface cross-linked superabsorbent particles and maintains channels for liquid flow. The plurality of second particles is typically electrostatically attracted to the superabsorbent polymer particles. The channels for liquid flow are at least partially maintained by the second particles because surface contact of the superabsorbent particles is inhibited.

In another embodiment, a liquid solidification system for reducing gel block includes a packet and a liquid solidifier. The packet is configured to allow liquid penetration. The liquid solidifier is initially located within the packet and includes a plurality of surface cross-linked superabsorbent polymer particles and a plurality of second particles. Liquid flow channels are defined between the superabsorbent polymer particles and the second particles.

The liquid flow channels may maintain permeability to allow for firm solidification of 3000 cc of fluid by about 90 grams of solidifier at a rate chosen from about 5 to 10 minutes.

The liquid flow channels may maintain permeability to allow for firm solidification of 1500 cc of fluid by about 45 grams of solidifier at a rate chosen from about 5 to 10 minutes.

The liquid flow channels may maintain permeability to allow for firm solidification of 1000 cc of fluid by about 30 grams of solidifier at a rate chosen from about 5 to 10 minutes.

The invention can also be considered as a method of solidifying liquid medical waste comprising:

placing a dissolvable film packet containing a population of surface cross-linked superabsorbent polymer particles and a plurality of second particles inside of a liquid medical waste collection vessel, wherein the second particles have an attraction to the superabsorbent polymer particles causing the second particles to partially coat the superabsorbent polymers and to lodge in the interstitial spaces between the superabsorbent polymer particles, introducing liquid medical waste into the liquid medical waste collection vessel, dissolving a portion of the packet in the liquid medical waste, releasing the second particles and the superabsorbent polymer particles from the dissolved portion of the packet and absorbing liquid medical waste into at least a portion of the released superabsorbent polymer particles, flowing liquid medical waste in channels formed by the interstitial spaces between the superabsorbent polymers and inhibiting full contact between the superabsorbent polymers, and firmly solidifying the liquid medical waste inside the medical waste collection vessel.

BRIEF DESCRIPTION OF THE DRAWINGS

The invention will be better understood by a reading of the Detailed Description of the Examples of the Invention along with a review of the drawings, in which.

DETAILED DESCRIPTION OF THE PREFERRED EMBODIMENTS

Figure 1:
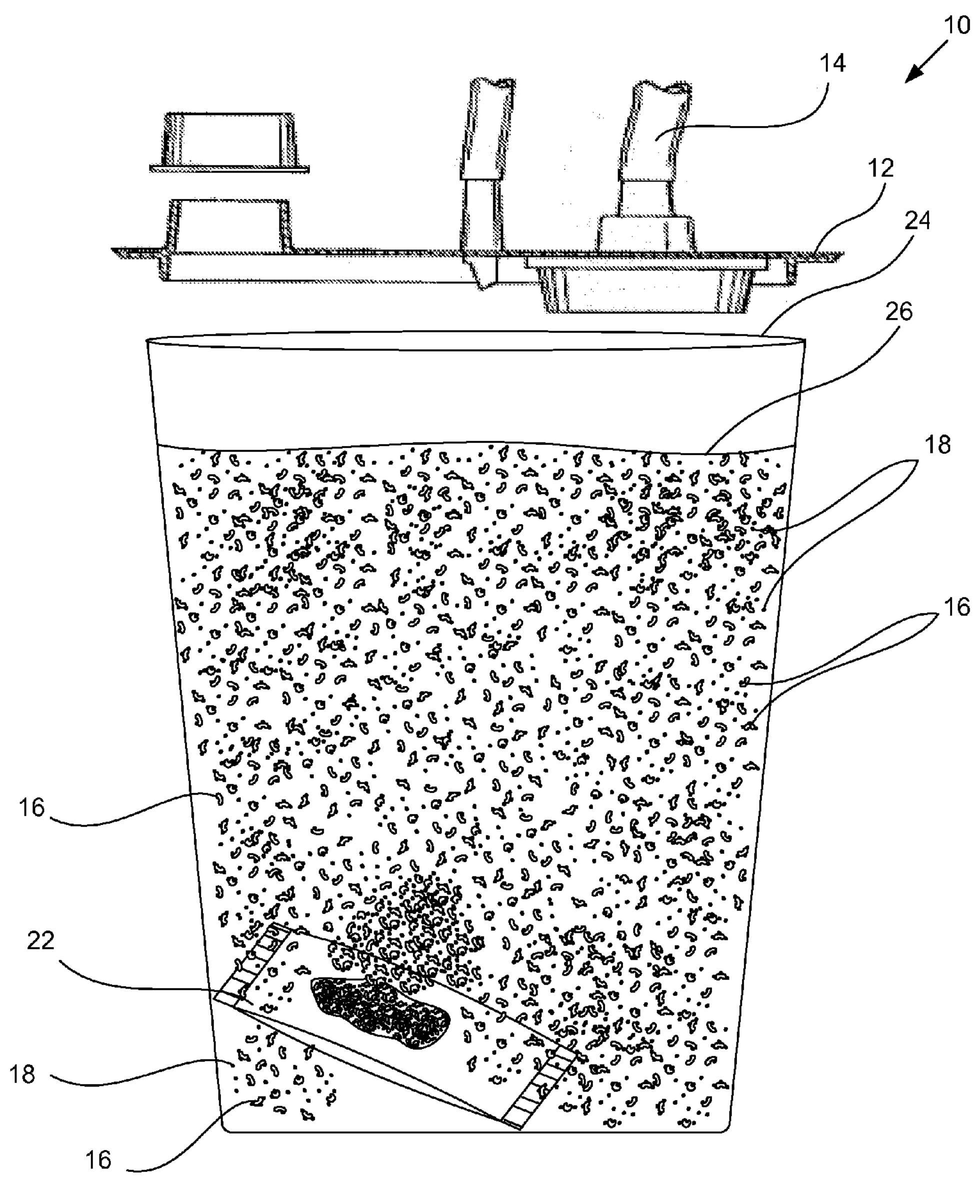
FIG. 1 is a perspective view of a system for solidification of liquid medical waste for use in connection with a vessel.

Referring now to the drawings in general, the illustrations are for the purpose of describing a preferred embodiment of the invention and are not intended to limit the invention thereto. FIG. 1 shows a system for solidification of liquid medical waste 10 including a medical waste collection container 24 having a lid 12 and a liquid supply line 14. Such canisters are conventional, and will not be discussed in detail. Examples of these can be seen in U.S. Pat. No. 6,797,857 to Tanhehco. The liquid medical waste is deposited in the vessel 24 under the influence of a suction, which directs the liquid through the conduit 14. The waste is usually an aqueous fluid mixture of saline, blood, urine, and/or other bodily fluids. Regulations require that the liquid be converted to a solidified form prior to transport in order to minimize the possibility of hazardous waste being spilled and superabsorbant polymers have been used to absorb and solidify liquid. However, development of "gel block" prohibits complete solidification. Gel block occurs when the inflowing aqueous mixture becomes solidified and sections off portions of the fluid so that it can not reach or be reached by available solidifier. When gel block occurs, the aqueous fluid does not firmly and completely solidify and spillage during transport is problematic.

As seen in FIG. 1, a packet 22 enclosing an absorbent composition may be placed inside of container 24. In one embodiment, the packet 22 is made of dissolvable polyvinyl alcohol; however, the packet made be made of any suitable water soluble film 23. The dissolvable portion of packet 22 should have disintegration time and temperature suitable to the fluids in which it will be exposed. Another consideration is compatibility of the packet 22 with its contents. Packet 22 should provide for prolonged storage capacity without resulting in insolubility, rigidity or changes in packet 22 or its contents. Examples of such compatible packets 22 are dissolvable films that can be acquired from MonoSol, LLC, such as their models M7031, M7061, M8534, and M8900 (PXP6829) of water soluble film. Optionally, water soluble paper may be used. Packet 22 may be made entirely of a dissolvable packet or may include a dissolvable portion. The dissolvability of packet 22 allows packet 22 to be placed into container 24 prior to introducing fluids into container 24. The dissolvable packets 22 provide a cost effective way to eliminate risk of exposure for medical workers and prevent handling of container 24 or lid 12 after fluids 26 have been introduced and while they are still liquid, as is necessary with powder or loose absorbents.

Figure 2:
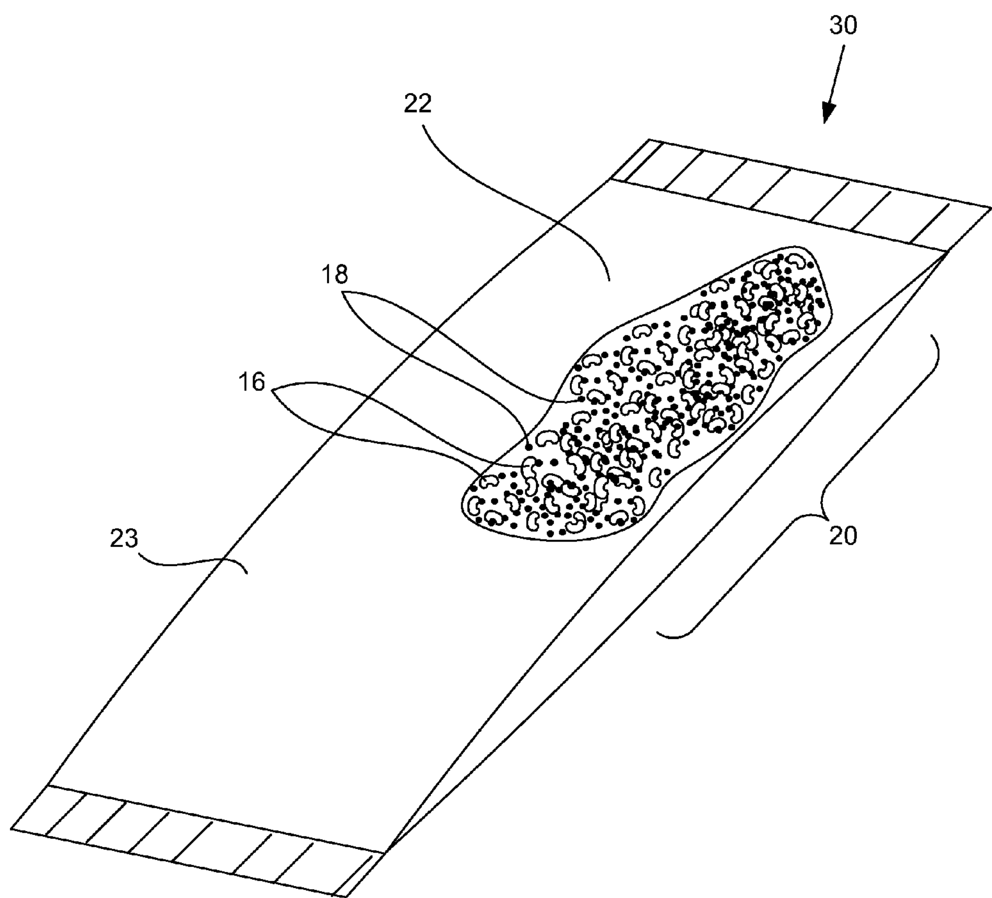
FIG. 2 is a perspective view of a packet containing an absorbent composition.

Enclosed within packet 22, in FIGS. 1 and 2, is a quantity of an absorbent composition 20 comprising a plurality of surface cross-linked superabsorbent particles 16 and a plurality of second particles 18. Cross-linked superabsorbent particles 16 are internally and surface cross-linked superabsorbent polymers as discussed in U.S. Pat. No. 7,291,674 to Kang, the entire disclosure is hereby incorporated by reference. A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers have one or both of internal crosslinking and surface crosslinking. Surface crosslinking is any process that increases the crosslink density of the polymer matrix in the vicinity of the superabsorbent particle surface with respect to the crosslinking density of the particle interior. Surface cross-linked superabsorbent polymers of the present invention are available from Stockhausen, Inc. of Greensboro, N. C. or from Zappa Tec, LLC of McLeansville, N. C., as AP95.

The plurality of second particles 18 may be inorganic, water-insoluble particles. In one embodiment, second particles 18 may be hydrophilic fumed silica as is offered by Evonik Industries as AEROSIL® 200. While not the preferred embodiment, other additives such as silicates, kaolin, zeolites and bentonite may be used.

After packet 22, with an enclosed absorbent composition 20, is placed inside container 24, then fluid 26 may be introduced without reopening or accessing container 24. As liquid is introduced into the container 24, packet 22 dissolves, releasing the absorbent composition 20. The absorbent composition 20 scatters throughout the aqueous liquid and the superabsorbent particles 16 absorb the liquid and the granular absorbent composition 20 becomes a gel-like substance as it solidifies the liquid.

The plurality of second particles 18 may reside on the surface of the superabsorbent particles 16 and become substantially interspaced between the superabsorbent particles 16. Second particles 18 may be attracted to the superabsorbent particles 16 by electrostatic forces.

Figure 3:
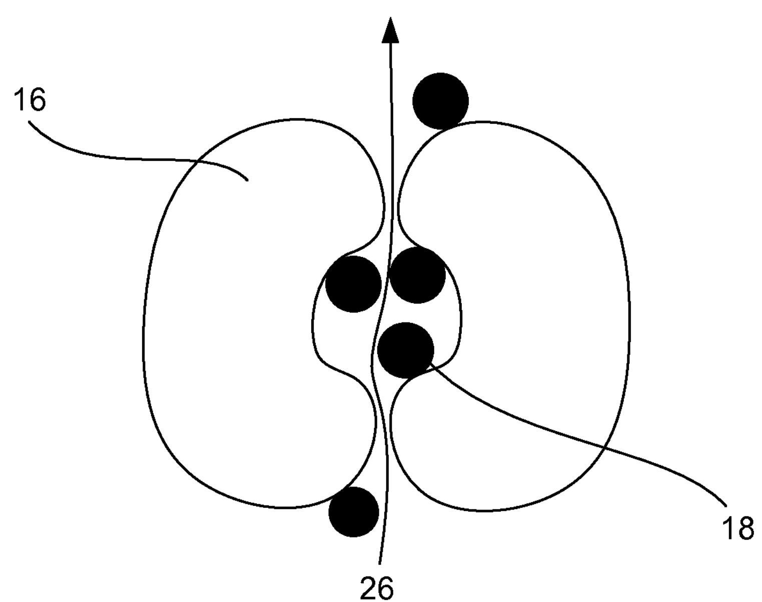
FIG. 3 is an illustration of flow channels between the surface cross-linked superabsorbent polymers.

As best seen in FIG. 3, the second particles 18 allow fuller and quicker liquid absorption by the superabsorbent particles 16 while inhibiting full surface touching of the superabsorbent particles 16. Additionally, the second particles 16 may reduce attractive forces between the superabsorbent particles and reduce a liquid film from developing between superabsorbent particles 16 that inhibits permeability. Due to the presence of the second particles 18 and the surface cross-linking of the superabsorbent particles 16, liquid flow channels 26 are maintained for a longer period of time between the superabsorbent particles. Thus, permeability of the gel is high as fluid is able to flow between the superabsorbent particles in the liquid flow channels 26 even after the particles 16 begin to swell. Additionally, swellablity of the superabsorbent particles is increased due to the presence of the second particles 18. The liquid flow channels 26 allow fluid to permeate the gel and flow to dry superabsorbent particles, thus reducing the chance of occurrence of the previously known problem of gel block in the process of solidification of liquid medical wastes.

As seen in FIG. 2, an absorbent composition 20 includes a population of superabsorbent polymer particles 16 having a majority of the population of superabsorbent polymer particles 16 each having a plurality of second particles 18 on their surfaces. Second particles 18 have been discussed above. An electrostatic attraction may exist between the second particles 18 and the superabsorbent polymer particles 16. The superabsorbent polymer particles 16 have diameters and surfaces and are cross-linked as discusses above. The second particles 18 have diameters that are substantially smaller than the diameters of the superabsorbent polymer particles 16. The plurality of second particles 18 prevent substantial contact between the superabsorbent polymer particles 16 and define channels 26 between the superabsorbent polymer particles allowing liquid penetration to the population of superabsorbent polymer particles 16 for absorption by the superabsorbent polymer particles 16. That is, the scope of the invention in a broad sense encompasses the use of such a population even without the dissolvable film packet. That is, in the broader interpretation, such a population dispersed differently into a container such as container 24 would be within the scope of the invention.

The absorbent composition 20 may include a sanitizer. Adding a sanitizer assists in further neutralizing the contaminants in the liquid medical waste, reducing handling risk. While any suitable granular sanitizer may be used, the sanitizer, by way of example, may be sodium dichloro-s-triazinetrione dihydrate known as ACL® 56 Chlorinating Composition and available from OxyChem® of Texas.

Additionally, this invention may be a liquid solidification system for reducing gel block including a packet and a liquid solidifier. The packet may be a dissolvable in fluids or may contain a dissolvable section. The liquid solidifier includes a plurality of surface cross-linked superabsorbent polymer particles 16 and a plurality of second particles 18 so that a plurality of liquid flow channels 26 are defined, as previously discussed. The packet may optionally be a bottle or any other suitable type of container.

The liquid solidification system may include at least 20 grams of the superabsorbent polymer particles per 1000 cc of fluid to be solidified and by weight/weight % a ratio of about 0.5% to 1.5% of the second particles per the superabsorbent polymer particles, preferably 1% second particles. Preferably, the system may include between 20 and 40 grams of the superabsorbent polymer particles per 1000 cc of fluid to be solidified. Additionally, the liquid solidification system may further include by weight/weight %, a ratio of about 5% to 15% of sanitizer per superabsorbent polymer particles, preferably 10%. When the sanitizer is added to the liquid solidification system, the system may include an additional by weight/weight % a ratio of about 10% to 20% of superabsorbent polymer particles to the original grams of superabsorbent polymer particles. The additional superabsorbent polymer was found to be beneficial to the solidification process when the sanitizer was added to ensure firm solidification in the presence of the sanitizer.

Dissolvable films were tested to determine optional dissolvable packs that maintain proper functionality with the addition of the sanitizer. Similar considerations as discussed above for the dissolvable film packs would apply here as well. Examples of such compatible packets 22 are dissolvable films that can be acquired from MonoSol, LLC, such as their models M7031 and M8900 (PXP6829) of water soluble film.

The invention may further be a method of solidifying liquid medical waste including: placing a dissolvable film packet containing a population of surface cross-linked superabsorbent polymer particles and a plurality of second particles inside of a liquid medical waste collection vessel. The second particles have an attraction to the superabsorbent polymer particles causing the second particles to partially coat the superabsorbent polymers and to lodge in the interstitial spaces between the superabsorbent polymer particles. Liquid medical waste is introduced into the liquid medical waste collection vessel and a portion of the packet dissolves in the liquid medical waste, releasing the second particles and the superabsorbent polymer particles from the dissolved portion of the packet. The released particles absorb liquid medical waste into at least a portion of the released superabsorbent polymer particles. Liquid medical waste flow in channels formed by the interstitial spaces between the superabsorbent polymers and the spaces inhibit full contact between the superabsorbent polymers. The result is to firmly solidify the liquid medical waste inside the medical waste collection vessel. Firm solidification is achieved when turning the medical waste collection vessel sideways results in no spillage of liquid medical waste.

Prior methods of releasing internally cross-linked superabsorbent polymer particles have been found to suffer from gel block due to the rapid swelling of the particles. Gel blocking occurs when the body of the absorbent forms a barrier layer of gel that keeps further liquid from contacting dry absorbent on a side of the gel away from the liquid. Such gel blocking may prevent the complete absorption of the liquid since the liquid to be absorbed is kept away from the dry absorbent by the gel barrier.

Surface cross-linked superabsorbent polymers have been found to increase the strength of the polymer-gel in sanitary articles such as diapers; however, increasing gel strength often decreases permeability, swellability and retention capacity of the superabsorbent polymer. While successfully applied in sanitary articles, absorption of medical fluids has the additional concern of gel block.

Non-soluble particles, such as silica, have been used to increase swellability in superabsorbent particles, and have in fact, been used with superabsorbent particles to obtain maximum swellability in order to cause water blocking (gel-block), as in fiber optic applications. Surprisingly, the inventors found that adding the non-soluble particles to the surface cross-linked superabsorbent polymer particles, increased swellability of the superabsorbent polymer particles but inhibited gel block, when combined to form a liquid solidifier for liquid medical wastes.

At the end of the medical procedure where liquid medical waste is gathered, the contents are turned into a firm gel, and the canister can be taken away for proper staging and ultimate disposal. Post procedure cleanup is streamlined, sanitary and time saving. The liquid solidifier in the packet is a much more efficiently packaged product as it is durable, easy to handle in the operating room setting and requires less shelf space than bottles of absorbent. Without bottles, no solid waste is generated. However, use of the particle combinations, previously discussed, dispersed from bottles or other containers is within the scope of the invention.

The particle combination provides full solidification, irrespective of how quickly fluid is introduced.

The particle combination inhibits the formation of gel block prior to firm solidification.

The particle combination reduces the time and risk of adding solidifier after waste fluid is introduced and the time and risk involved with post procedure handling.

The particle combination as packaged in the packet 22 saves on storage space.

Certain modifications and improvements will occur to those skilled in the art upon reading the foregoing description. It should be understood that all such modifications and improvements have been omitted for the sake of conciseness and readability, but are properly within the scope of the following claims. For example, although the primary intended use is for liquid medical waste, other aqueous liquids could be solidified. Also, although the film is preferably all dissolvable, it is within the scope of the invention to make only parts dissolvable.

What is claimed is:

1. An absorbent composition comprising a population of superabsorbent polymer particles that have diameters and surfaces and that are cross-linked internally and on their surfaces, a majority of the population of superabsorbent polymer particles each having a plurality of second particles on the surfaces of the superabsorbent polymer particles, the second particles having diameters substantially smaller than the diameters of the superabsorbent polymer particles, whereby the plurality of second particles prevent substantial contact between the superabsorbent polymer particles and define channels between the superabsorbent polymer particles to allow liquid penetration to the population of superabsorbent polymer particles for absorption by the superabsorbent polymer particles, and a granular chlorine sanitizer.

2. The absorbent composition as claimed in claim 1, wherein the second particles are electrostatically attracted to the surfaces of the superabsorbent polymer particles.

3. The absorbent composition as claimed in claim 1, wherein the second particles are inorganic non-soluble particles.

4. The absorbent composition as claimed in claim 1, wherein the second particles are fumed silica.

5. A system for solidification of liquid medical waste for use in connection with a vessel configured to receive an aqueous liquid to be solidified comprising:

an absorbent composition, the absorbent composition being granular and comprising:

a plurality of surface cross-linked superabsorbent particles, and a plurality of second particles, wherein the second particles become interspaced between the surface cross-linked superabsorbent particles and maintain channels for liquid flow by inhibiting full-surface touching between the surface cross-linked superabsorbent particles, the plurality of second particles being electrostatically attracted to the plurality of surface cross-linked superabsorbent particles, a packet made of dissolvable polyvinyl alcohol enclosing the absorbent composition, the packet being at least partially soluble in the aqueous liquid to be solidified so that the absorbent composition is released upon dissolution of the packet.

6. A liquid solidification system for reducing gel block, the system comprising:

a packet made of dissolvable polyvinyl alcohol configured to allow a liquid penetration; and a granular liquid solidifier initially located within the packet, the solidifier comprising:

a plurality of surface cross-linked superabsorbent polymer particles; and a plurality of second particles positioned so that a plurality of liquid flow channels are defined between the plurality of super-absorbent polymer particles and second particles.

7. The liquid solidification system as claimed in claim 6, wherein the liquid solidifier comprises:

at least 20 grams of the superabsorbent polymer particles per 1000 cc of fluid to be solidified.

8. The liquid solidification system as claimed in claim 7, wherein the liquid solidifier further includes by weight/weight %, a ratio of about 0.5% to 1.5% of the second particles.

9. The liquid solidification system as claimed in claim 8, further including by weight/weight % ratio of about 5% to 15% of sanitizer.

10. The liquid solidification system as claimed in claim 9, further including an additional by weight/weight % ratio of about 10% to 20% of superabsorbent polymer particles added to the liquid solidifier.

11. The liquid solidification system as claimed in claim 6, wherein the liquid flow channels maintain permeability to allow for firm solidification of 3000 cc of fluid at a rate chosen from 5 to 10 minutes.

12. The liquid solidification system as claimed in claim 6, wherein the liquid flow channels maintain permeability to allow for firm solidification of 1500 cc of fluid at a rate chosen from 5 to 10 minutes.

13. The liquid solidification system as claimed in claim 6, wherein the liquid flow channels maintain permeability to allow for firm solidification of 1000 cc of fluid at a rate chosen from 5 to 10 minutes.

* * * * *